(12) United States Patent
Tagawa et al.

(10) Patent No.: US 10,721,839 B2
(45) Date of Patent: Jul. 21, 2020

(54) RADIOGRAPHIC APPARATUS

(71) Applicant: CANON KABUSHIKI KAISHA, Tokyo (JP)

(72) Inventors: Motoki Tagawa, Chigasaki (JP); Yohei Saito, Kawasaki (JP); Satoru Omura, Chigasaki (JP); Youjirou Hiratsuka, Yokohama (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 31 days.

(21) Appl. No.: 16/149,292

(22) Filed: Oct. 2, 2018

(65) Prior Publication Data

US 2019/0110376 A1 Apr. 11, 2019

(30) Foreign Application Priority Data

Oct. 6, 2017 (JP) ................. 2017-196204

(51) Int. Cl.
 *H05K 7/20* (2006.01)
 *G01T 1/20* (2006.01)
 *G01T 1/24* (2006.01)
 *A61B 6/00* (2006.01)
 *G01T 1/202* (2006.01)

(52) U.S. Cl.
 CPC ....... *H05K 7/20436* (2013.01); *A61B 6/4488* (2013.01); *G01T 1/202* (2013.01); *G01T 1/2006* (2013.01); *G01T 1/2018* (2013.01); *G01T 1/244* (2013.01)

(58) Field of Classification Search
 CPC ... H05K 7/20436; G01T 1/2018; G01T 1/202; G01T 1/244; G01T 1/2006; A61B 6/4488
 See application file for complete search history.

(56) References Cited

U.S. PATENT DOCUMENTS

| 5,811,790 | A | 9/1998 | Endo et al. |
| 9,275,770 | B2 | 3/2016 | Omura |
| 9,295,438 | B2 | 3/2016 | Omura et al. |
| 9,433,394 | B2 * | 9/2016 | Omura ................. A61B 6/5205 |
| 10,024,980 | B2 | 7/2018 | Suzuki et al. |
| 10,061,042 | B2 | 8/2018 | Suzuki et al. |
| 10,073,180 | B2 | 9/2018 | Kobayashi et al. |
| 2006/0065848 | A1 * | 3/2006 | Ueno ................... A61B 6/037 250/370.15 |

(Continued)

FOREIGN PATENT DOCUMENTS

| JP | 3957803 B2 | 8/2007 |
| JP | 2012181238 A | 9/2012 |
| JP | 2015200606 A | 11/2015 |

*Primary Examiner* — Michael C Bryant
(74) *Attorney, Agent, or Firm* — Venable LLP

(57) ABSTRACT

A radiographic apparatus of the present invention includes a radiation sensor configured to convert incident radiation into an image signal; a base supporting the radiation sensor; an electronic component, electrically connected to the radiation sensor, that generates heat by being driven; a casing containing the radiation sensor, the base and the electronic component; a heat transfer member disposed in an opposite side to the base across the electronic component, and configured to transfer the heat generated from the electronic component to the casing; and a support member supporting the base and the heat transfer member.

24 Claims, 6 Drawing Sheets

(56) References Cited

U.S. PATENT DOCUMENTS

| | | | |
|---|---|---|---|
| 2012/0138798 A1* | 6/2012 | Kato | H01L 27/14618 |
| | | | 250/336.1 |
| 2012/0195404 A1 | 8/2012 | Omura | |
| 2014/0098942 A1 | 4/2014 | Omura et al. | |
| 2015/0342553 A1 | 12/2015 | Sato et al. | |
| 2016/0161616 A1* | 6/2016 | Nakayama | G01T 1/244 |
| | | | 250/370.15 |
| 2016/0252629 A1 | 9/2016 | Hiratsuka et al. | |
| 2019/0018151 A1* | 1/2019 | Kawaguchi | G01T 1/2018 |

\* cited by examiner

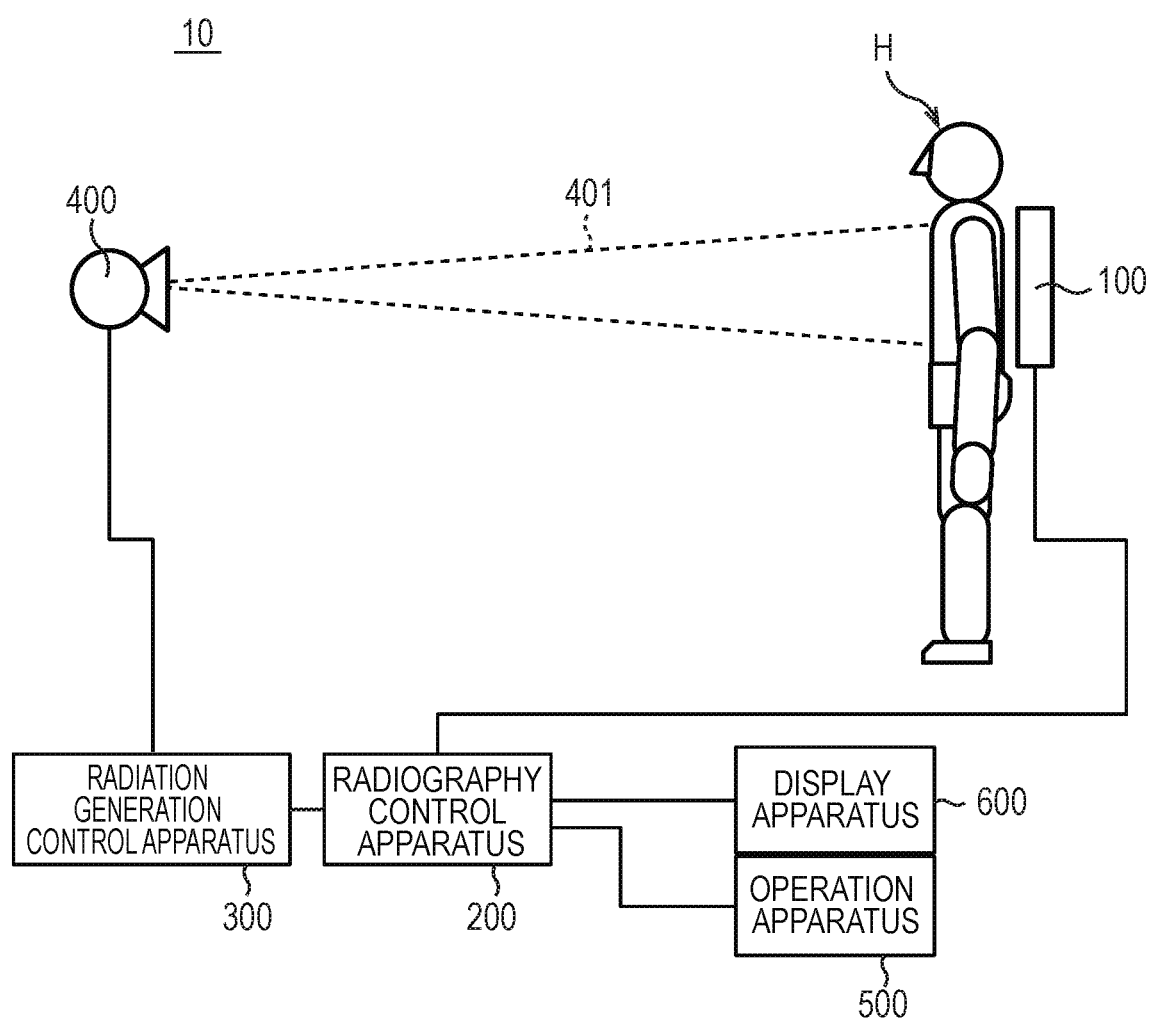

RADIOGRAPHIC APPARATUS

BACKGROUND OF THE INVENTION

Field of the Invention

The present invention relates to a radiographic apparatus.

Description of the Related Art

As radiographic apparatuses used for medical image diagnosis and nondestructive inspection, apparatuses which acquire digital radiographic images using a radiation sensor have come into mainstream use in recent years.

In general, electronic components are built into such a radiographic apparatus, for controlling imaging operation, processing taken images, and performing other relevant operations. Operation of such electronics component generates heat. When the temperature of the radiation sensor becomes uneven across the plane thereof due to the generated heat, this can cause a taken image to suffer unevenness. Therefore, the heat generated is needed to be efficiently discharged outside the effective region of the radiation sensor. On this point, Japanese Patent No. 3957803 discusses a technology of suppressing a temperature increase of a radiation sensor by providing a heat conduction member thermally connecting between an electronic component as a heat source and a casing.

Meanwhile, the radiographic apparatuses are being made small and light in weight, and even portable radiographic apparatuses have been being put into practical use. Such a portable radiographic apparatus can image a subject in any posture, which enables radiography in an ordinary sick room, an outdoor environment and the like. Meanwhile, the portable radiographic apparatus needs sufficient strength so as not to break due to its accidental falling or the like during its use. On this point, Japanese Patent Application Laid-Open No. 2012-181238 discusses a technology of improving withstand load by forming a recess part in the casing of a radiographic apparatus. Moreover, Japanese Patent Application Laid-Open No. 2015-200606 discusses a technology of protecting a radiation sensor by providing a buffer material between the casing and the radiation sensor of the radiographic apparatus.

When an impact load or a static load is locally exerted from the outside of the casing, low rigidity of the casing causes local deformation on the casing. For example, a radiographic apparatus will be considered in which a heat conduction member is provided between an electronic component as a heat source and a casing with heat tolerance of the apparatus taken into account. For such an apparatus, the aforementioned local deformation on the casing results in load to be exerted on the electronic component as the heat source, which causes factors of breakage of the electronic component and increase of noise thereof. Even the technologies discussed in Japanese Patent Application Laid-Open No. 2012-181238 and Japanese Patent Application Laid-Open No. 2015-200606 do not provide sufficient measures in view of withstand load for an electronic component as a heat source as above.

The present invention is devised in view of the aforementioned problems, and an object thereof is to provide a radiographic apparatus with which heat tolerance of the apparatus is secured and withstand load for a heat-generating electronic component is improved.

SUMMARY OF THE INVENTION

A radiographic apparatus of the present invention includes: a radiation sensor configured to convert incident radiation into an image signal; a base supporting the radiation sensor; an electronic component, electrically connected to the radiation sensor, that generates heat by being driven; a casing containing the radiation sensor, the base and the electronic component; a heat transfer member disposed in an opposite side to the base across the electronic component, and configured to transfer heat generated from the electronic component to the casing; and a support member supporting the base and the heat transfer member.

Further features of the present invention will become apparent from the following description of exemplary embodiments with reference to the attached drawings.

BRIEF DESCRIPTION OF THE DRAWINGS

FIG. 1 is a diagram exemplarily illustrating a schematic configuration of a radiographic system including a radiographic apparatus according to a first embodiment of the present invention.

FIG. 2A is an elevation view of the radiographic apparatus as seen from an incident surface of radiation. FIG. 2B is a cross-sectional view taken along the line A-A illustrated in FIG. 2A.

FIG. 3A is a cross-sectional view taken along the line A-A illustrated in FIG. 2A. FIG. 3B is a plan view of the configuration illustrated in FIG. 3A as seen from a rear casing side which is the surface opposite to the incident surface which the radiation is incident on.

FIG. 4A is a cross-sectional view taken along the line A-A illustrated in FIG. 2A. FIG. 4B is a plan view of the configuration illustrated in FIG. 4A as seen from the rear casing side which is the surface opposite to the incident surface which the radiation is incident on.

FIG. 5A is a diagram corresponding to a cross-sectional view taken along the line A-A illustrated in FIG. 2A. FIG. 5B is a plan view of the configuration illustrated in FIG. 5A as seen from the rear casing 120 side which is the surface opposite to the incident surface which the radiation is incident on.

FIG. 6A is an elevation view of the radiographic apparatus as seen from the rear casing side which is the surface opposite to the incident surface which the radiation is incident on. FIG. 6B is a cross-sectional view of the radiographic apparatus illustrated in FIG. 6A.

DESCRIPTION OF THE EMBODIMENTS

Figure 2A:
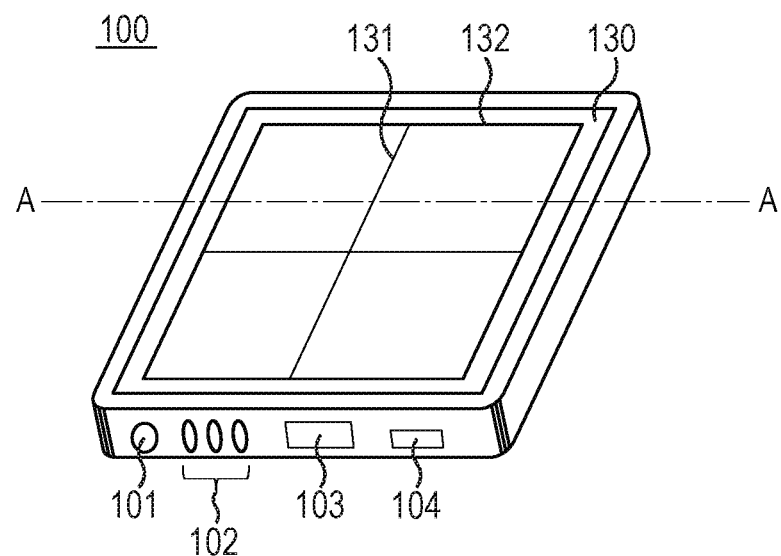
FIGS. 2A and 2B are diagrams, illustrating the first embodiment of the present invention, exemplarily illustrating a schematic configuration of the radiographic apparatus.

Preferred embodiments of the present invention will now be described in detail in accordance with the accompanying drawings.

For the following embodiments of the present invention, radiographic apparatuses which image a subject using radiation are described. Examples of the radiation include α-rays, β-rays, γ-rays, particle rays and cosmic rays as well as X-rays.

First Embodiment

First, a first embodiment of the present invention is described.

FIG. 1 is a diagram exemplarily illustrating a schematic configuration of a radiographic system 10 including a radiographic apparatus 100 according to the first embodiment of the present invention.

As illustrated in FIG. 1, the radiographic system 10 has the radiographic apparatus 100, a radiography control apparatus 200, a radiation generation control apparatus 300, a radiation generation apparatus 400, an operation apparatus 500 and a display apparatus 600.

The radiographic system 10 generates radiation 401 toward a subject (subject to be examined in the example illustrated in FIG. 1) H from the radiation generation apparatus 400, and detects the radiation 401 by the radiographic apparatus 100 to take a digital radiographic image (hereafter called "taken image") according to the subject H. The radiographic system 10 performs imaging based on an inspection order including a plurality of items of inspection information input, for example, from the operation apparatus 500. The inspection information includes imaging protocol information. Imaging protocols define one of parameter information and imaging performance information which are used in imaging, image processing or the like, and imaging environment information such, for example, as a radiation sensor type and an imaging posture. The inspection information also includes one of information for specifying an inspection order and information for specifying a taken image according to the inspection order, such as an inspection ID and a reception number.

The radiographic apparatus 100 detects the radiation 401 emitted from the radiation generation apparatus 400 to radiograph the subject H, and generates a taken image according to the subject H, based on control of the radiography control apparatus 200. Specifically, the radiographic apparatus 100 detects the radiation 401 transmitted through the subject H as a charge corresponding to the quantity of the transmitted radiation to generate the taken image.

The radiography control apparatus 200 performs control and various kinds of processing according to radiography of the subject H, for example, based on information input from the operation apparatus 500. Specifically, for example, the radiography control apparatus 200 integrally controls radiography processing based on the aforementioned imaging protocols. Moreover, the radiography control apparatus 200 performs various kinds of image processing on the taken image obtained from the radiographic apparatus 100. Such image processing includes, for example, gradation processing and frequency processing, and is performed using image processing parameters according to the imaging protocols. Furthermore, the radiography control apparatus 200 performs display control for displaying a taken image obtained through the image processing and various kinds of information on the display apparatus 600.

The radiation generation control apparatus 300 performs control of the radiation generation apparatus 400 based on control of the radiography control apparatus 200. Specifically, the radiation generation control apparatus 300 controls the radiation generation apparatus 400 to generate the radiation 401 based on the imaging protocols, according to control of the radiography control apparatus 200. More in detail, the radiation generation control apparatus 300 applies voltage to the radiation generation apparatus 400 and causes the radiation generation apparatus 400 to generate the radiation 401 according to imaging conditions corresponding to the imaging protocols (parameters such, for example, as a tube current, a tube voltage and an irradiation time).

The radiation generation apparatus 400 generates the radiation 401 toward the subject H based on control of the radiation generation control apparatus 300. In the example illustrated in FIG. 1, the radiation generation apparatus 400 includes a radiographic tube (X-ray tube).

The operation apparatus 500 is operated when various kinds of information are input to the radiography control apparatus 200, for example, by an operator. The operation apparatus 500 includes, for example, a keyboard, a mouse and various kinds of buttons.

The display apparatus 600 displays the taken image and various kinds of information based on control of the radiography control apparatus 200. The display apparatus 600 includes, for example, a display. The display apparatus 600 can also display, for example, one of an inspection order received from an external apparatus and an inspection order input through the operation apparatus 500 by the operator.

Figure 2B:
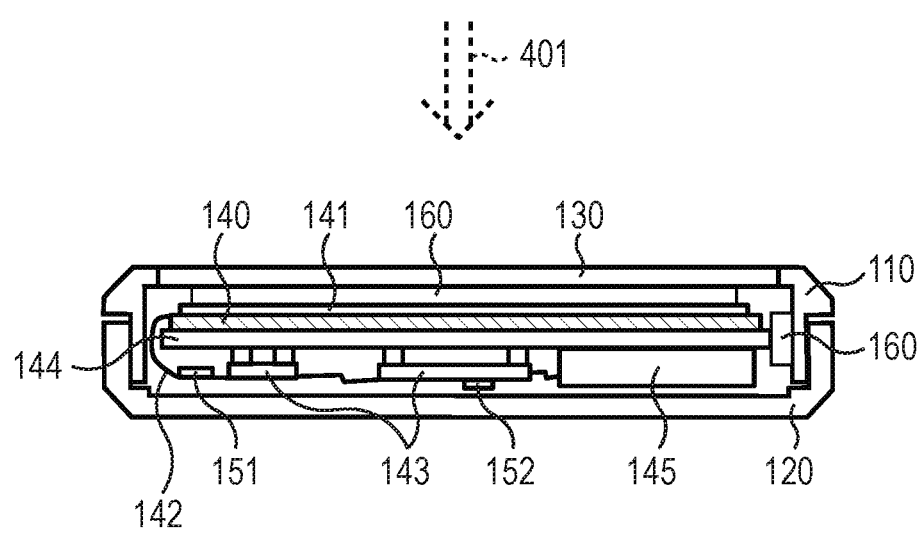

FIGS. 2A and 2B are diagrams, illustrating the first embodiment of the present invention, exemplarily illustrating a schematic configuration of the radiographic apparatus 100 illustrated in FIG. 1. Specifically, FIG. 2A is an elevation view of the radiographic apparatus 100 as seen from the incident surface of the radiation 401. FIG. 2B is a cross-sectional view taken along the line A-A illustrated in FIG. 2A.

A casing of the radiographic apparatus 100 includes a front casing 110, a rear casing 120 and a radiation transmission plate 130 illustrated in FIG. 2B. As illustrated in FIG. 2B, the radiation transmission plate 130 is provided on the incident surface, of the radiographic apparatus 100, which the radiation 401 is incident on. As illustrated in FIG. 2B, the rear casing 120 is provided on a surface of the radiographic apparatus 100 opposite to the incident surface (radiation transmission plate 130) which the radiation 401 is incident on. As illustrated in FIG. 2B, the front casing 110 is provided between the radiation transmission plate 130 and the rear casing 120. The front casing 110 and the rear casing 120 in the casing of the radiographic apparatus 100 are formed, for example, of low specific gravity materials such as aluminum, magnesium and CFRP. Thereby, their weights can be reduced to secure strength against falling thereof and impact thereon and to reduce load in transportation thereof. The radiation transmission plate 130 in the casing of the radiographic apparatus 100 is formed, for example, of a material such as CFRP. As illustrated in FIG. 2A, the radiation transmission plate 130 is given an index 131 indicating the center position of reading of a sensor panel 140 illustrated in FIG. 2B, and an index 132 indicating the range of reading of the sensor panel 140 illustrated in FIG. 2B.

Moreover, as illustrated in FIG. 2A, the radiographic apparatus 100 includes, on its lateral surface, a switch 101, a state display part 102, a wireless communication part 103 and a wired communication connection part 104. Moreover, as illustrated in FIG. 2B, a battery 145 is provided inside the radiographic apparatus 100. The battery 145 may be easily detachably attached so as to be exchanged for a charged battery in the case of its small residual capacity. The radiographic apparatus 100 performs imaging using the battery 145 as a power supply and communicates with the radiography control apparatus 200 through the wireless communication part 103, and thereby, it can be used in a wireless manner. In the case of poor wireless connection or the similar case, the communication may be performed in a wired manner in connection to the wired communication connection part 104 with a cable (not illustrated). Power can also be supplied in a wired manner in the case of shortage of the battery 145 in residual capacity or the similar case. The switch 101 can be used for operation of switching on/off the power supply of the radiographic apparatus 100, operation of switching the state of whether or not imaging can be performed (readiness of imaging), and the similar operation. The state display part 102 displays the state where the power supply is turned on/off, the residual capacity of the battery 145, and the like by the color of light, the state where the light is turned on/blinking/turned off, and the like.

As illustrated in FIG. 2B, the casing of the radiographic apparatus 100 contains the sensor panel 140, a fluorescent substance 141, a flexible circuit board 142, electric circuit boards 143, a base 144, the battery 145, integrated circuits 151 and 152, and buffer materials 160.

The sensor panel 140 includes a plurality of photoelectric transducers, for example, on a glass substrate. The fluorescent substance 141 is provided on the surface of the sensor panel 140 on the photoelectric transducer side, and converts the incident radiation 401 into visible light. The fluorescent substance 141 is formed, for example, of a material such as CsI. The radiation 401 incident on the radiographic apparatus 100 allows the fluorescent substance 141 to emit light. The light is converted into a charge (image signal) by each photoelectric transducer of the sensor panel 140. Each charge (image signal) is used for generating the taken image.

In the present embodiment, the sensor panel 140 and the fluorescent substance 141 constitute a radiation sensor that converts the incident radiation 401 into an image signal. The sensor panel 140 and the fluorescent substance 141 constituting the radiation sensor are supported on the base 144. While for the present embodiment, an example is presented in which the sensor panel 140 and the fluorescent substance 141 constitute the radiation sensor, the present invention is not limited to this mode. For example, the present invention can also be embodied in a mode of using a direct conversion sensor, such as an a-Se sensor, which directly converts the radiation 401 into a charge (image signal) as the aforementioned radiation sensor.

The sensor panel 140 is electrically connected to the integrated circuit 151 implemented on the flexible circuit board 142 via the flexible circuit board 142. The charge (image signal) generated by the sensor panel 140 is output to the integrated circuit 151 via the flexible circuit board 142. The integrated circuit 151 amplifies a small amount of charge (image signal), and through A/D conversion and the like, generates a digital image signal. The integrated circuit 151 is electrically connected to the integrated circuit 152 implemented on the electric circuit board 143. The integrated circuit 152 acquires the digital image signal from the integrated circuit 151, and through various kinds of signal processing on this digital image signal, outputs the obtained signal to the radiography control apparatus 200. Moreover, the integrated circuit 152 has various functions of driving the radiographic apparatus 100, controlling charging, and the like as well as the function of the signal processing on the digital image signal.

In the present embodiment, the integrated circuit 151 and the integrated circuit 152 constitute an electronic component that is electrically connected to the radiation sensor and generates heat by being driven.

The base 144 with rigidity is bonded onto the surface side of the sensor panel 140 opposite to the incident surface of the radiation 401. Thereby, the sensor panel 140 can be prevented from suffering deformation or cracks due to load from the outside, vibration during transportation and the like. Moreover, onto the base 144, a radiation shielding member (not illustrated) is attached as needed, which is to suppress the electric circuit board 143 from deteriorating due to radiation, to remove scattered rays from behind the radiographic apparatus 100, and to similarly function. The radiation shielding member is formed, for example, of a high specific gravity material such as molybdenum, iron and lead.

The buffer materials 160 are properly provided between the casing of the radiographic apparatus 100 and the components therein. They can lead to an effect of dispersing load from the outside and an effect of buffering impact. The buffer materials 160 are formed, for example, of any of silicone- or urethane-based foam materials, silicone gel materials, and the like.

As mentioned above, the integrated circuits 151 and the integrated circuit 152 generate heat by being driven, which causes their temperatures to rise. When the temperatures of the integrated circuits 151 and 152 rise too high, this can cause breakage of each integrated circuit. Moreover, when the temperature of the sensor panel 140 becomes uneven across the plane thereof, this can cause the taken image to suffer unevenness. Therefore, the present embodiment employs a configuration which transfers the heat to the casing of the radiographic apparatus 100 to discharge the heat to the outside of the radiographic apparatus 100.

Figure 3A:
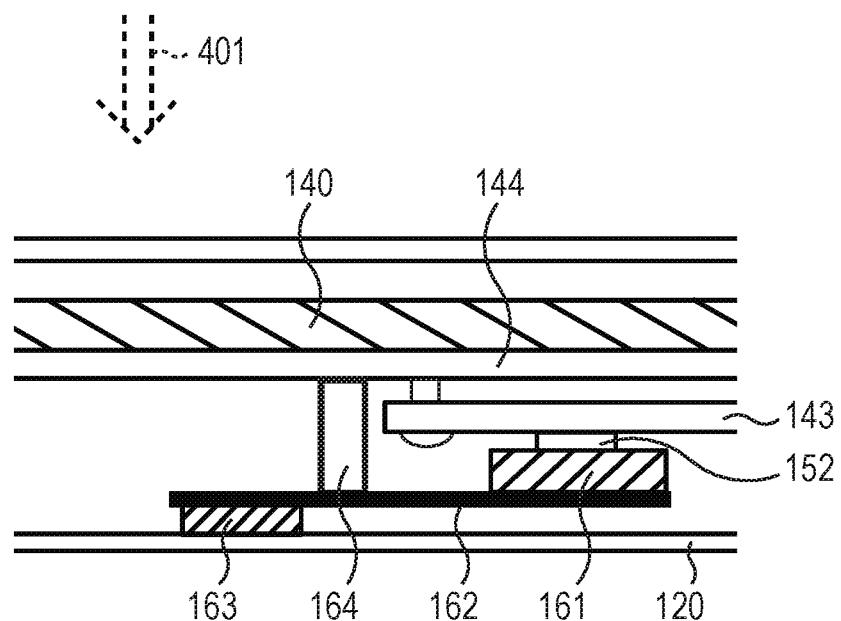
FIGS. 3A and 3B are diagrams, illustrating the first embodiment of the present invention, illustrating a first exemplary configuration of the radiographic apparatus.
Figure 3B:
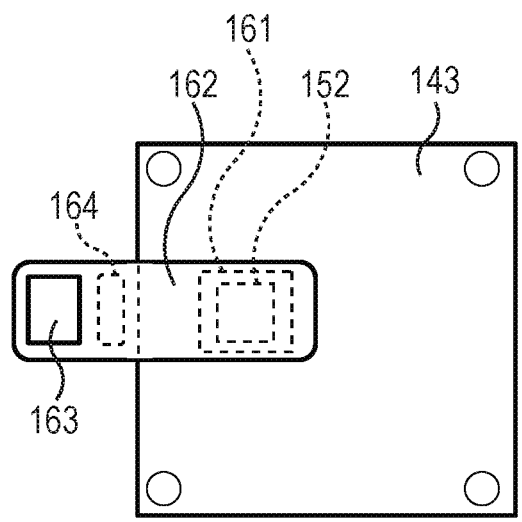

FIGS. 3A and 3B are diagrams, illustrating the first embodiment of the present invention, illustrating a first exemplary configuration of the radiographic apparatus 100 illustrated in FIG. 1. In FIGS. 3A and 3B, the similar configurations to the configurations illustrated in FIGS. 2A and 2B are given the same signs and their detailed description is omitted. FIGS. 3A and 3B illustrate a partial region according to the periphery of the integrated circuit 152 of the radiographic apparatus 100 illustrated in FIGS. 2A and 2B. In FIGS. 3A and 3B, certain configurations (fluorescent substance 141 and the like) are omitted and certain configurations (components 161 to 164) are added as needed. Specifically, FIG. 3A is a cross-sectional view taken along the line A-A illustrated in FIG. 2A. FIG. 3B is a plan view of the configuration illustrated in FIG. 3A as seen from the rear casing 120 side which is the surface opposite to the incident surface (radiation transmission plate 130) which the radiation 401 is incident on.

A heat absorption member 161 is a heat absorption member that absorbs heat generated through heat generation by the integrated circuit 152 as a heat source. A heat conduction plate 162 is a heat conduction member that conducts the heat absorbed by the heat absorption member 161. A heat discharge member 163 is a heat discharge member that discharges the heat conducted by the heat conduction plate 162 to the casing of the radiographic apparatus 100 (rear casing 120 in the example illustrated in FIGS. 3A and 3B). In the present embodiment, the heat absorption member 161, the heat conduction plate 162 and the heat discharge member 163 are provided on the integrated circuit as a heat source (integrated circuit 152 in the example illustrated in FIGS. 3A and 3B) in the opposite direction to the direction in which the base 144 is disposed. They constitute a heat transfer member that transfers heat generated through heat generation by the integrated circuit to the casing of the radiographic apparatus 100.

A support 164 is a support member that supports the base 144 and the aforementioned heat transfer member (heat conduction plate 162 in the example illustrated in FIGS. 3A and 3B).

Hereafter, the configuration illustrated in FIGS. 3A and 3B is specifically described.

The integrated circuit 152 is in contact with the heat absorption member 161 and the like. The heat absorption member 161 absorbs heat generated through heat generation by the integrated circuit 152. The heat conduction plate 162 is in contact with the heat absorption member 161, the heat discharge member 163 and the support 164, and conducts the heat absorbed by the heat absorption member 161 to the heat discharge member 163. The heat discharge member 163 is in contact with the heat conduction plate 162 and the rear casing 120, and discharges the heat conducted by the heat conduction plate 162 to the rear casing 120. Thereby, the heat generated by the integrated circuit 152 can be discharged to the rear casing 120 via the heat absorption member 161, the heat conduction plate 162 and the heat discharge member 163. Thus, heat tolerance of the radiographic apparatus 100 can be secured and improved.

For the heat absorption member 161 and the heat discharge member 163, for example, a silicone rubber sheet, a heat conductive grease, and an adhesive agent for heat radiation are used. For the heat conduction plate 162, for example, a material with high thermal conductivity is used, such as aluminum and copper. The present invention can also be applied to a mode of discharging heat generated by the integrated circuit 152 to the rear casing 120 in which mode the heat absorption member 161 and the heat discharge member 163 are removed and the heat conduction plate 162 is brought into direct contact with the integrated circuit 152 and the rear casing 120.

Now, as illustrated in FIG. 3B, the heat absorption member 161 and the heat discharge member 163 are disposed at positions where they do not overlap with each other as seen from the rear casing 120 side (the same holds true for the case as seen from the radiation transmission plate 130 side which is the incident surface which the radiation 401 is incident on). As illustrated in FIG. 3B, the support 164 is disposed in a region between the heat absorption member 161 and the heat discharge member 163 as seen from the rear casing 120 side (the same holds true for the case as seen from the radiation transmission plate 130 side which is the incident surface which the radiation 401 is incident on).

As illustrated in FIG. 3A, the support 164 supports the base 144 and the heat conduction plate 162. For the support 164, for example, a press-fitting nut or an integrally molded rib provided on the base 144 is used. In particular, when a material with heat insulation is used for the support 164, heat can be more efficiently discharged to the rear casing 120 positioned on the backside of the radiographic apparatus 100.

When load is exerted from the outside of the rear casing 120, the rear casing 120 deforms and the heat discharge member 163 is pressed inward. The support 164 functions as a fulcrum of the heat conduction plate 162 in this stage, and thereby outward load is transmitted to the heat absorption member 161, which allows no new load to be exerted on the integrated circuit 152. This can realize a configuration in which load is hardly transmitted to the integrated circuit 152. Withstand load for the integrated circuit 152 can be improved. The improvement of the withstand load for the integrated circuit 152 can suppress breakage and noise generation of the integrated circuit 152. Furthermore, when the heat conduction plate 162 is fixed to the support 164 by screw fastening or the like, the support 164 can suppress a rotational displacement of the heat conduction plate 162. This allows even the outward load not to be exerted on the heat absorption member 161. Thereby, contact pressure between the heat absorption member 161 and the integrated circuit 152 can be made unchanged, and heat can be stably discharged even when load is being exerted from the outside.

Figure 4A:
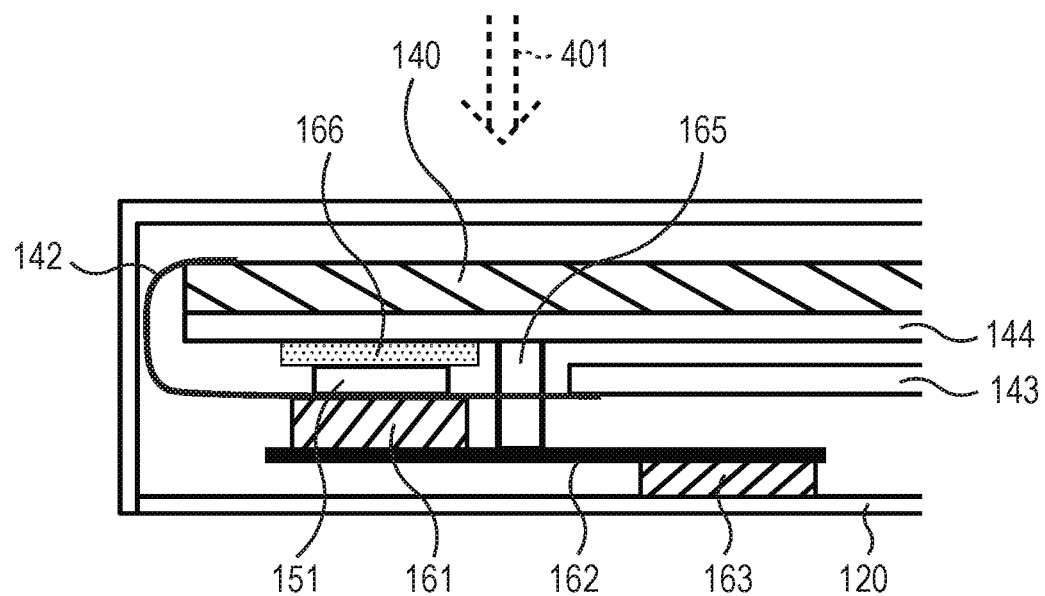
FIGS. 4A and 4B are diagrams, illustrating the first embodiment of the present invention, illustrating a second exemplary configuration of the radiographic apparatus.
Figure 4B:
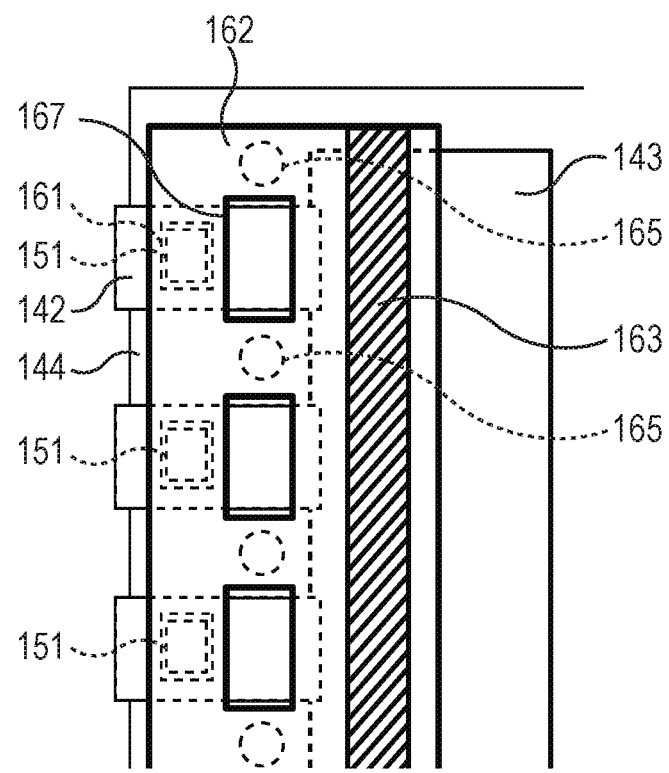

FIGS. 4A and 4B are diagrams, illustrating the first embodiment of the present invention, illustrating a second exemplary configuration of the radiographic apparatus 100 illustrated in FIG. 1. In FIGS. 4A and 4B, the similar configurations to the configurations illustrated in FIGS. 2A to 3B are given the same signs and their detailed description is omitted. FIGS. 4A and 4B illustrate a partial region according to the periphery of the integrated circuits 151 implemented on the flexible circuit board 142 of the radiographic apparatus 100 illustrated in FIGS. 2A and 2B. In FIGS. 4A and 4B, certain configurations (fluorescent substance 141 and the like) are omitted and certain configurations (components 161 to 163, 165 and 166) are added as needed. Specifically, FIG. 4A is a cross-sectional view taken along the line A-A illustrated in FIG. 2A. FIG. 4B is a plan view of the configuration illustrated in FIG. 4A as seen from the rear casing 120 side which is the surface opposite to the incident surface (radiation transmission plate 130) which the radiation 401 is incident on.

The heat absorption member 161, the heat conduction plate 162 and the heat discharge member 163 illustrated in FIGS. 4A and 4B respectively have the similar functions to those of the heat absorption member 161, the heat conduction plate 162 and the heat discharge member 163 illustrated in FIGS. 3A and 3B. Supports 165 illustrated in FIGS. 4A and 4B have the similar function to that of the support 164 illustrated in FIGS. 3A and 3B.

Similarly to the integrated circuit 152, the integrated circuit 151 is connected to the heat conduction plate 162 via the heat absorption member 161. The heat conduction plate 162 is connected to the rear casing 120 via the heat discharge member 163. Thereby, heat generated by the integrated circuit 151 can be discharged to the rear casing 120 via the heat absorption member 161, the heat conduction plate 162 and the heat discharge member 163. FIG. 4A illustrates a heat insulation member 166 configured between the integrated circuit 151 and the base 144. For the heat insulation member 166, for example, a foam resin is used. Providing the heat insulation member 166 can suppress the generated heat of the integrated circuit 151 from being transmitted to the sensor panel 140. This can suppress the taken image from suffering unevenness or the like due to a temperature increase of the sensor panel 140. Moreover, the heat insulation member 166 also achieve an effect of suppressing the flexible circuit board 142 from bending due to pressing load of the heat absorption member 161.

As illustrated in FIGS. 4A and 4B, the integrated circuits 151 are continuously arranged parallel to a side, of the sensor panel 140, to which the flexible circuit board 142 is connected (hereafter called "flexible side"). The periphery of the flexible side tends to suffer temperature increase. Therefore, it is efficient to release the heat in a direction perpendicular to the flexible side (right/left direction in FIG. 4B) as seen from the rear casing 120 side (the same holds true for the case as seen from the radiation transmission plate 130 side which is the incident surface which the radiation 401 is incident on) as illustrated in FIG. 4B. This can release the heat to a portion low in temperature. For this reason, the heat discharge member 163 is disposed on the opposite side to the flexible side relative to the integrated circuits 151 as seen from the rear casing 120 side (the same holds true for the case as seen from radiation transmission plate 130 side which is the incident surface which the radiation 401 is incident on).

Approximately ten flexible circuit boards 142 are provided on one side of the sensor panel 140 to read image signals. Gaps between these circuit boards are not more than approximately 30 mm. The supports 165 supporting the base 144 and the heat conduction plate 162 are arranged at the gaps between the circuit boards as illustrated in FIG. 4B. In the present embodiment, while the supports 165 can be provided on the electric circuit board 143, the supports 165 may be arranged at the aforementioned gaps since they can prevent load from being exerted on the electric circuit board 143.

In the heat conduction plate 162, an opening part 167 is provided in a region not in contact with the support 165 and between a portion in contact with the heat absorption member 161 and a portion in contact with the heat discharge member 163. Specifically, in FIG. 4B, the opening parts 167 are provided between portions supported on the supports 165. When load is exerted from the outside of the rear casing 120, the rear casing 120 deforms and the heat discharge members 163 are pressed inward. Providing the opening parts 167 leads to the arrangement of the supports 165 on transmission paths of the force which is caused by the heat discharge members 163 pressed inward. Thus, the supports 165 function as fulcrums, which allows no new load to be exerted on the integrated circuits 151. Namely, providing the opening parts 167 can more improve withstand load for the integrated circuits 151. Notably, no opening parts 167 can be provided when deflections between the supports 165 can be ignored. This comes in one of the case where the heat conduction plate 162 has sufficient rigidity and the distances between the supports 165 are sufficiently short and the case where the heat discharge member 163 is sufficiently separated from the supports 165.

According to the radiographic apparatus 100 according to the first embodiment described above, heat tolerance of the apparatus can be secured, and withstand load for the integrated circuits 151 and 152 which are heat-generating electronic components can be improved. There can be therefore suppressed breakage and noise generation of the integrated circuits 151 and 152 due to external load.

Second Embodiment

Next, a second embodiment of the present invention is described. In the following description of the second embodiment, the portions common to those of the aforementioned first embodiment are omitted therefrom and portions different from those of the aforementioned first embodiment are described.

A schematic configuration of the radiographic system 10 according to the second embodiment is similar to the schematic configuration of the radiographic system 10 according to the first embodiment illustrated in FIG. 1. Moreover, a schematic configuration of a radiographic apparatus according to the second embodiment is similar to the schematic configuration of the radiographic apparatus 100 according to the first embodiment illustrated in FIGS. 2A and 2B. The second embodiment is a mode taking it into account that heat generated by the integrated circuits 151 is efficiently discharged by the casing of the radiographic apparatus 100 and taking the similar factor into account.

Figure 5A:
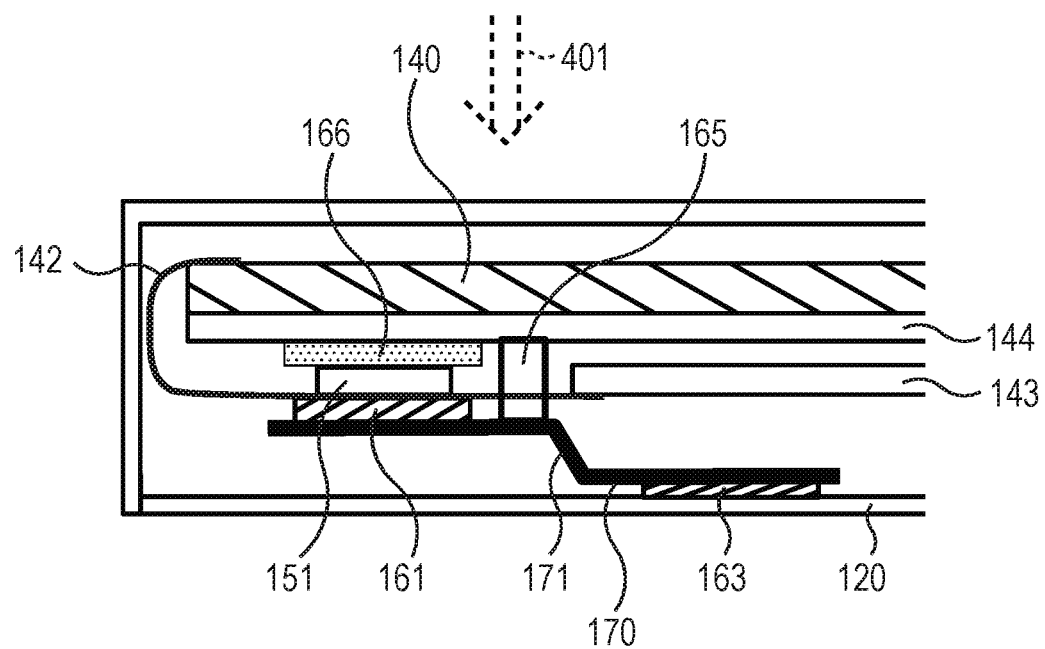
FIGS. 5A and 5B are diagrams, illustrating a second embodiment of the present invention, illustrating an exemplary configuration of the radiographic apparatus.
Figure 5B:
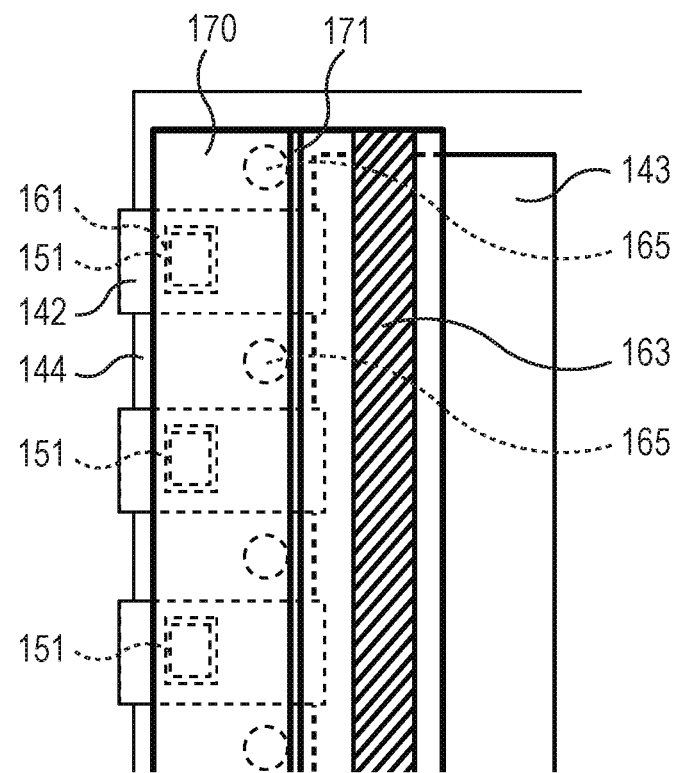

FIGS. 5A and 5B are diagrams, illustrating the second embodiment of the present invention, illustrating an exemplary configuration of the radiographic apparatus 100 illustrated in FIG. 1. In FIGS. 5A and 5B, the similar configurations to the aforementioned configurations illustrated in FIGS. 2A to 4B are given the same signs and their detailed description is omitted. FIGS. 5A and 5B illustrate a partial region according to the periphery of the integrated circuits 151 implemented on the flexible circuit board 142 of the radiographic apparatus 100 illustrated in FIGS. 2A and 2B. In FIGS. 5A and 5B, certain configurations (fluorescent substance 141 and the like) are omitted and certain configurations (components 161, 163, 165, 166 and 170) are added as needed. Specifically, FIG. 5A is a cross-sectional view taken along the line A-A illustrated in FIG. 2A. FIG. 5B is a plan view of the configuration illustrated in FIG. 5A as seen from the rear casing 120 side which is the surface opposite to the incident surface (radiation transmission plate 130) which the radiation 401 is incident on.

The heat absorption member 161 and the heat discharge member 163 illustrated in FIGS. 5A and 5B respectively have the similar functions to those of the heat absorption member 161 and the heat discharge member 163 illustrated in FIGS. 4A and 4B. The supports 165 illustrated in FIGS. 5A and 5B have the similar function to that of the support 164 illustrated in FIGS. 4A and 4B. The heat insulation member 166 illustrated in FIG. 5A has the similar function to that of the heat insulation member 166 illustrated in FIG. 4A.

In the second embodiment, in place of the heat conduction plate 162 of the first embodiment illustrated in FIGS. 4A and 4B, a heat conduction plate 170 illustrated in FIGS. 5A and 5B is employed. In the second embodiment, the heat absorption member 161, the heat conduction plate 170 and the heat discharge member 163 are provided on the integrated circuit as a heat source (integrated circuit 151 in the example illustrated in FIGS. 5A and 5B) in the opposite direction to the direction in which the base 144 is disposed. They constitute the heat transfer member which transfers heat generated through heat generation by the integrated circuit to the casing of the radiographic apparatus 100.

As illustrated in FIG. 5A, in the heat conduction plate 170, a step-shaped bent part 171 is provided in a region not in contact with the supports 165 and between a portion in contact with the heat absorption member 161 and a portion in contact with the heat discharge member 163. Specifically, in the example illustrated in FIG. 5A, the step-shaped bent part 171 is bent in a direction in which the portion in contact with the heat discharge member 163 recedes from the base 144 relative to the portion in contact with the heat absorption member 161.

Specifically, as illustrated in FIGS. 5A and 5B, the step-shaped bent part 171 is provided parallel to the flexible side of the sensor panel 140, and formed in a direction of approaching the rear casing 120 from the integrated circuits 151. Providing the step-shaped bent part 171 can make the thicknesses of the heat absorption member 161 and the heat discharge member 163 small. Heat can be more efficiently discharged therethrough. Moreover, providing the step-shaped bent part 171 enhances rigidity of the heat conduction plate 170 between the supports 165. Therefore, the step-shaped bent part 171 can suppress deflections between the supports when the heat discharge member 163 is pressed inward. Thus, the straight line connecting the supports 165 functions as a fulcrum, which allows no new load to be exerted on the integrated circuits 151. In the second embodiment, the opening parts 167 in the first embodiment illustrated in FIG. 4B are able not to be provided due to the combination of the supports 165 and the step-shaped bent part 171. No opening parts 167 can lead to a large area of the heat conduction plate 162, which enables more efficient heat discharge.

Notably, also in the radiographic apparatus 100 according to the second embodiment, the configuration illustrated in FIGS. 3A and 3B can be employed as the configuration according to the periphery of the integrated circuit 152.

According to the radiographic apparatus 100 according to the second embodiment, heat generated by the integrated circuits 151 which are heat-generating electronic components can be more efficiently discharged in addition to the aforementioned effects in the first embodiment.

Third Embodiment

Next, a third embodiment of the present invention is described. In the following description of the third embodiment, the portions common to those of the aforementioned first embodiment and second embodiment are omitted therefrom and portions different from those of the aforementioned first embodiment and second embodiment are described.

A schematic configuration of the radiographic system 10 according to the third embodiment is similar to the schematic configuration of the radiographic system 10 according to the first embodiment illustrated in FIG. 1. The third embodiment is a mode taking portability of the radiographic apparatus 100 and the like into account.

Figure 6A:
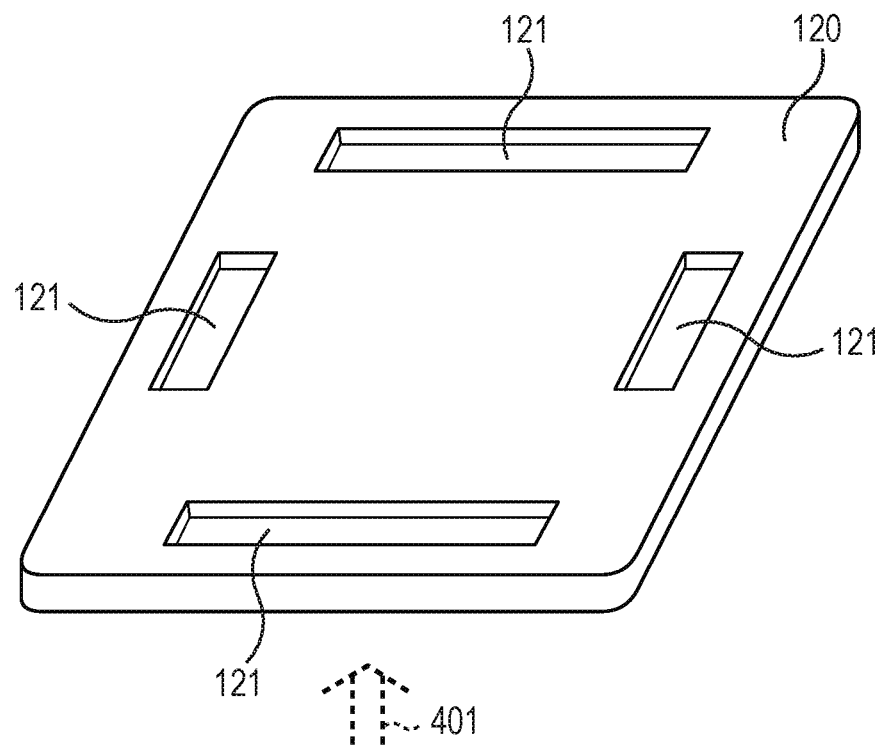
FIGS. 6A and 6B are diagrams, illustrating a third embodiment of the present invention, exemplarily illustrating a schematic configuration of the radiographic apparatus.
Figure 6B:
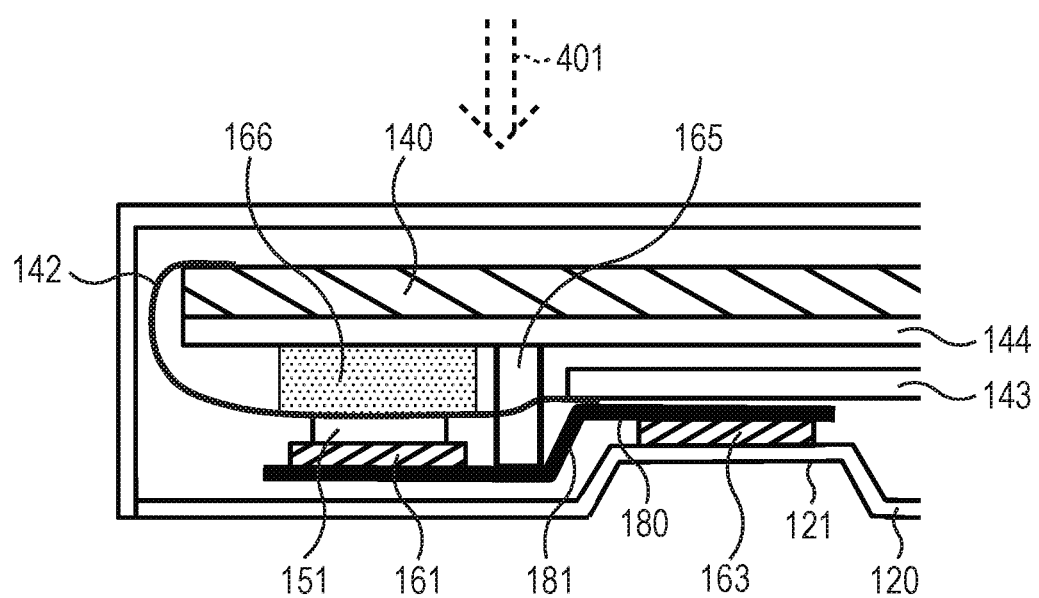

FIGS. 6A and 6B are diagrams, illustrating the third embodiment of the present invention, exemplarily illustrating a schematic configuration of the radiographic apparatus 100 illustrated in FIG. 1. Specifically, FIG. 6A is an elevation view of the radiographic apparatus 100 as seen from the rear casing 120 side which is the surface opposite to the incident surface (radiation transmission plate 130 illustrated in FIG. 2A) which the radiation 401 is incident on. FIG. 6B is a cross-sectional view of the radiographic apparatus 100 illustrated in FIG. 6A.

As illustrated in FIG. 6A, in the rear casing 120, recess parts 121 for holding are provided on the surface opposite to the incident surface which the radiation 401 is incident on. Providing the recess parts 121 enables to hold the radiographic apparatus 100 with fingers into those when carrying it, which can improve convenience. Deeper recess parts 121 are better. The distances of the recess parts 121 from the end faces are desirably approximately 20 mm to 40 mm.

FIG. 6B illustrates a cross-sectional view of the radiographic apparatus 100 similarly to the FIG. 5A, and therein, the similar configurations to those in FIG. 5A are given the same signs. In the third embodiment, in place of the heat conduction plate 170 of the second embodiment illustrated in FIG. 5A, a heat conduction plate 180 illustrated in FIG. 6B is employed. In the third embodiment, the heat absorption member 161, the heat conduction plate 180 and the heat discharge member 163 are provided on the integrated circuit as a heat source (integrated circuit 151 in the example illustrated in FIG. 6B) in the opposite direction to the direction in which the base 144 is disposed. They constitute the heat transfer member which transfers heat generated through heat generation by the integrated circuit to the casing of the radiographic apparatus 100.

As illustrated in FIG. 6B, in the heat conduction plate 180, a step-shaped bent part 181 is provided in a region not in contact with the support and between a portion in contact with the heat absorption member 161 and a portion in contact with the heat discharge member 163. Specifically, in the example illustrated in FIG. 6B, the step-shaped bent part 181 is bent in a direction in which the portion in contact with the heat discharge member 163 approaches the base 144 relative to the portion in contact with the heat absorption member 161.

The heat absorption member 161, the heat discharge member 163, the support 165 and the heat insulation member 166 illustrated in FIG. 6B respectively have the similar functions to those of the heat absorption member 161, the heat discharge member 163, the support 165 and the heat insulation member 166 illustrated in FIG. 5A.

The integrated circuit 151 is disposed outward of the recess part 121 (on the side of the flexible side) as seen from the incident direction of the radiation 401. Since a shorter distance between the sensor panel 140 and the integrated circuit 151 along the flexible circuit board 142 can make the influence of noise smaller, the integrated circuit 151 is disposed as outward as possible (more outer on the casing than the recess part 121).

The step-shaped bent part 181 of the heat conduction plate 180 is provided parallel to the flexible side between the recess part 121 and the integrated circuit 151 as seen from the incident direction of the radiation 401, and formed in a direction of approaching the base 144 from the integrated circuit 151. Providing the step-shaped bent part 181 enables the integrated circuit 151 to be disposed separate from the base 144, and can make the heat insulation member 166 thick. The influence of heat on the sensor panel 140 can be made small. Moreover, providing the step-shaped bent part 181 can make the depth of the recess part 121 large regardless of the position, in height, of the integrated circuit 151. Furthermore, providing the step-shaped bent part 181 enhances rigidity of the heat conduction plate 180 between the supports 165. Therefore, the step-shaped bent part 181 can suppress deflections between the supports 165 when the heat discharge member 163 is pressed inward. The straight line connecting the supports 165 functions as a fulcrum, which allows no new load to be exerted on the integrated circuit 151.

Notably, also in the radiographic apparatus 100 according to the third embodiment, the configuration illustrated in FIGS. 3A and 3B can be employed as the configuration according to the periphery of the integrated circuit 152.

According to the radiographic apparatus 100 according to the third embodiment, the similar effects to those in the first embodiment mentioned above are achieved.

According to the present invention, heat tolerance of the apparatus can be secured, and withstand load for a heat-generating electronic component can be improved.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2017-196204, filed Oct. 6, 2017, which is hereby incorporated by reference herein in its entirety.

What is claimed is:
1. A radiographic apparatus comprising:
 a radiation sensor configured to convert incident radiation into an image signal;
 a base supporting the radiation sensor;
 an electronic component, electrically connected to the radiation sensor, that generates heat by being driven;

a casing containing the radiation sensor, the base and the electronic component;
a heat transfer member disposed so as to sandwich the electronic component with the base, and configured to transfer the heat generated from the electronic component to the casing; and
a support member supporting the base and the heat transfer member,
wherein the heat transfer member includes a heat absorption member configured to absorb the heat, a heat conduction member configured to conduct the heat absorbed by the heat absorption member, and a heat discharge member configured to discharge the heat conducted by the heat conduction member to the casing, and
wherein for the heat conduction member, a step-shaped bent part is provided in a region not in contact with the support member and between a portion in contact with the heat absorption member and a portion in contact with the heat discharge member.

2. The radiographic apparatus according to claim 1, wherein the step-shaped bent part is bent in one of a direction in which the portion in contact with the heat discharge member approaches the base relative to the portion in contact with the heat absorption member and a direction in which the portion in contact with the heat discharge member recedes from the base relative to the portion in contact with the heat absorption member.

3. The radiographic apparatus according claim 2, wherein the heat transfer member transfers the heat to a surface of the casing opposite to an incident surface which the radiation is incident on.

4. The radiographic apparatus according to claim 1, further comprising a heat insulation member between the radiation sensor and the electronic component.

5. The radiographic apparatus according to claim 1, wherein
a recess part for holding is provided on a surface of the casing opposite to an incident surface which the radiation is incident on, and
the electronic component is disposed more outward of the casing than the recess part as seen from the incident surface side.

6. The radiographic apparatus according to claim 1, wherein the casing includes a radiation transmission plate disposed on an incident surface of the radiation, a rear casing disposed on a surface opposite to the incident surface, and a front casing disposed between the radiation transmission plate and the rear casing, and
the heat transfer member transfers the heat generated through the heat generation by the electronic component to the rear casing.

7. The radiographic apparatus according to claim 6, wherein the rear casing is formed of CFRP.

8. The radiographic apparatus according to claim 1, wherein the heat conduction member is formed of metal.

9. The radiographic apparatus according to claim 1, wherein the heat absorption member and the heat discharge member are formed of an adhesive agent for heat radiation.

10. The radiographic apparatus according to claim 9, wherein each of the heat absorption member and the heat discharge member is formed of one of a silicone rubber sheet and a heat conductive grease.

11. The radiographic apparatus according to claim 1, wherein the support member is formed of a heat insulative material.

12. The radiographic apparatus according to claim 11, wherein the heat conduction member is fixed to the support member by screw fastening.

13. The radiographic apparatus according claim 1, wherein the heat transfer member transfers the heat to a surface of the casing opposite to an incident surface which the radiation is incident on.

14. The radiographic apparatus according to claim 1, wherein the heat absorption member, the heat discharge member, and the support member are arranged at positions that do not overlap each other when viewed from the incident surface side of the radiation sensor.

15. A radiographic apparatus comprising:
a radiation sensor configured to convert incident radiation into an image signal;
a base supporting the radiation sensor;
an electronic component, electrically connected to the radiation sensor, that generates heat by being driven;
a casing containing the radiation sensor, the base and the electronic component;
a heat transfer member disposed so as to sandwich the electronic component with the base, and configured to transfer the heat generated from the electronic component to the casing; and
a support member supporting the base and the heat transfer member,
wherein the heat transfer member includes a heat absorption member configured to absorb the heat, a heat conduction member configured to conduct the heat absorbed by the heat absorption member, and a heat discharge member configured to discharge the heat conducted by the heat conduction member to the casing, and
wherein in the heat conduction member, an opening part is provided in a region not in contact with the support member and between a portion in contact with the heat absorption member and a portion in contact with the heat discharge member.

16. The radiographic apparatus according claim 15, wherein the heat transfer member transfers the heat to a surface of the casing opposite to an incident surface which the radiation is incident on.

17. The radiographic apparatus according to claim 15, further comprising a heat insulation member between the radiation sensor and the electronic component.

18. The radiographic apparatus according to claim 15, wherein a recess part for holding is provided on a surface of the casing opposite to an incident surface which the radiation is incident on, and the electronic component is disposed more outward of the casing than the recess part as seen from the incident surface side.

19. The radiographic apparatus according to claim 15, wherein the casing includes a radiation transmission plate disposed on an incident surface of the radiation, a rear casing disposed on a surface opposite to the incident surface, and a front casing disposed between the radiation transmission plate and the rear casing, and the heat transfer member transfers the heat generated through the heat generation by the electronic component to the rear casing.

20. The radiographic apparatus according to claim 15, wherein the heat conduction member is formed of metal.

21. The radiographic apparatus according to claim 15, wherein the heat absorption member and the heat discharge member are formed of an adhesive agent for heat radiation.

22. The radiographic apparatus according to claim 15, wherein the support member is formed of a heat insulative material.

23. The radiographic apparatus according to claim 15, wherein the heat absorption member, the heat discharge member, and the support member are arranged at positions that do not overlap each other when viewed from the incident surface side of the radiation sensor.

24. A radiographic apparatus comprising:
- a radiation sensor configured to convert incident radiation into an image signal;
- a base supporting the radiation sensor;
- an electronic component, electrically connected to the radiation sensor, that generates heat by being driven;
- a casing containing the radiation sensor, the base and the electronic component;
- a heat transfer member disposed so as to sandwich the electronic component with the base, and configured to transfer the heat generated from the electronic component to the casing; and
- a support member supporting the base and the heat transfer member,
- wherein the heat transfer member includes a heat absorption member configured to absorb the heat, a heat conduction member configured to conduct the heat absorbed by the heat absorption member, and a heat discharge member configured to discharge the heat conducted by the heat conduction member to the casing,
- wherein the support member supports the base and the heat conduction member; and
- wherein the heat transfer member transfers the heat to a surface of the casing opposite to an incident surface which the radiation is incident on.

* * * * *